United States Patent
Leclere-Bienfait et al.

(10) Patent No.: US 10,688,142 B2
(45) Date of Patent: Jun. 23, 2020

(54) **METHODS OF TREATMENT USING A LIPID EXTRACT OF *PASSIFLORA* SEEDS CONCENTRATED IN ITS UNSAPONIFIABLE FRACTION**

(71) Applicant: Laboratoires Expanscience, Paris la Défense (FR)

(72) Inventors: Sophie Leclere-Bienfait, Dreux (FR); Stephanie Bredif, Croisilles (FR); Sebastien Debrock, Saint-Martin-de Nigelles (FR); Sebastien Garnier, Le Rouret (FR)

(73) Assignee: LABORATOIRES EXPANSCIENCE, Paris la Defense (FR)

( * ) Notice: Subject to any disclaimer, the term of this patent is extended or adjusted under 35 U.S.C. 154(b) by 0 days.

(21) Appl. No.: 16/243,491

(22) Filed: Jan. 9, 2019

(65) Prior Publication Data

US 2019/0209631 A1 Jul. 11, 2019

Related U.S. Application Data

(62) Division of application No. 15/023,893, filed as application No. PCT/EP2014/070463 on Sep. 25, 2014, now abandoned.

(30) Foreign Application Priority Data

Sep. 25, 2013 (FR) ...................................... 13 59252

(51) Int. Cl.
| | | |
|---|---|---|
| A61K 36/185 | (2006.01) |
| A61Q 19/00 | (2006.01) |
| A61Q 19/08 | (2006.01) |
| A61K 8/97 | (2017.01) |
| A23L 33/105 | (2016.01) |
| A61Q 19/06 | (2006.01) |
| A61K 9/00 | (2006.01) |
| A61K 9/06 | (2006.01) |
| A61K 9/107 | (2006.01) |
| A23D 9/007 | (2006.01) |
| C11B 3/00 | (2006.01) |
| A61P 17/02 | (2006.01) |
| A61K 8/31 | (2006.01) |
| A61K 8/36 | (2006.01) |
| A61K 8/63 | (2006.01) |
| A61K 8/67 | (2006.01) |
| A61K 8/92 | (2006.01) |
| A61K 31/01 | (2006.01) |
| A61K 31/20 | (2006.01) |
| A61K 31/201 | (2006.01) |
| A61K 31/202 | (2006.01) |
| A61K 31/355 | (2006.01) |
| A61K 31/56 | (2006.01) |
| A61Q 19/04 | (2006.01) |
| C11B 3/02 | (2006.01) |
| C11B 3/12 | (2006.01) |

(52) U.S. Cl.
CPC ............ *A61K 36/185* (2013.01); *A23D 9/007* (2013.01); *A23L 33/105* (2016.08); *A61K 8/31* (2013.01); *A61K 8/361* (2013.01); *A61K 8/63* (2013.01); *A61K 8/678* (2013.01); *A61K 8/922* (2013.01); *A61K 8/97* (2013.01); *A61K 9/0014* (2013.01); *A61K 9/06* (2013.01); *A61K 9/107* (2013.01); *A61K 31/01* (2013.01); *A61K 31/20* (2013.01); *A61K 31/201* (2013.01); *A61K 31/202* (2013.01); *A61K 31/355* (2013.01); *A61K 31/56* (2013.01); *A61P 17/02* (2018.01); *A61Q 19/00* (2013.01); *A61Q 19/004* (2013.01); *A61Q 19/007* (2013.01); *A61Q 19/04* (2013.01); *A61Q 19/06* (2013.01); *A61Q 19/08* (2013.01); *C11B 3/001* (2013.01); *C11B 3/006* (2013.01); *C11B 3/02* (2013.01); *C11B 3/12* (2013.01); *A23V 2002/00* (2013.01); *A61K 2236/55* (2013.01); *A61K 2800/592* (2013.01); *A61K 2800/80* (2013.01)

(58) Field of Classification Search
None
See application file for complete search history.

(56) References Cited

U.S. PATENT DOCUMENTS

| | | | |
|---|---|---|---|
| 5,262,163 | A | 11/1993 | Rancurel |
| 9,452,190 | B2 * | 9/2016 | Samach ............... A61K 36/185 |
| 2011/0159074 | A1 | 6/2011 | Warren et al. |

(Continued)

FOREIGN PATENT DOCUMENTS

EP 1541158 A1 6/2005

OTHER PUBLICATIONS

Matsui Y. et al. Extract of Passion Fruit Seed Containging High Amounts of Piceatannol Inhibits Melanogenesis and Promotes Collagen Synthesis. J of Agricultural and Food Chemistry 58(2)11112-8, Oct. 27, 2010. (Year: 2010).*

(Continued)

*Primary Examiner* — Ralph J Gitomer
(74) *Attorney, Agent, or Firm* — Potomac Law Group, PLLC

(57) ABSTRACT

A method to treat skin or mucosa cells or disorders related to dermal tissue by topically administering to a person in a need thereof a lipid extract from *Passiflora* seeds selected from *Passiflora incarnate* seeds, *Passiflora edulis* seeds, and a combination thereof, wherein said lipid extract is oil of *Passiflora* seeds concentrated in its unsaponifiable fraction containing 3 to 100 weight % of unsaponifiables relative to the total weight of the extract.

17 Claims, 1 Drawing Sheet

(56) References Cited

U.S. PATENT DOCUMENTS

| | | | | |
|---|---|---|---|---|
| 2015/0374605 | A1* | 12/2015 | Msika | A61K 31/23 424/59 |
| 2016/0074312 | A1* | 3/2016 | Msika | A61K 45/06 424/59 |
| 2016/0235794 | A1* | 8/2016 | Leclere-Bienfait | A23L 33/105 |
| 2019/0000902 | A1* | 1/2019 | Leclere-Bienfait | A61K 8/498 |

OTHER PUBLICATIONS

Matsui Y. et al. Seeking a New Anti-Sin-Aging Material. ACS Symposium Series 1129(Tropical and Subtropical Fruits) 189-202, 2013. (Year: 2013).*

Mori, S. et al. The Effect of Passion Fruit Seeds Extract That Contains Piceatannol. Free Radical Biology and Medicine 53(Suppl 2) S110 #259, Nov. 1, 2012. (Year: 2012).*

Winitchai P. et al. The Study of Appropriate Extraction Methods and Analysis Composition of Passion Fruit Seed Oil. Proceedings of the 45th Kasetsart Univ. Annual Conference pp. 664-672, 2007. (Year: 2007).*

Liu S. et al. Physical and Chemical Analysis of Passiflora Seeds and Seed Oil from China. Int J of Food Sciences and Nutrition 59(7-8)706-715, 2008. (Year: 2008).*

Embree N. The Separation of Natural Components of Fats and Oils by Molecular Distillation. Chemical Reviews 29(2)317-332, Oct. 1941. (Year: 1941).*

AarhusKarishamn Sweden AB, "Lipex Omega Passiflora," Aug. 2008, retrieved from online at: http://www.aak.com/Global/Products/Beauty%20and%20personal%20care/Emollients-Omega%20Oils/aak-lfc_lipex_omega_Passiflora_0808.pdf.

Carvalho De Santana et al., "Chemical Composition and Antioxidant Capacity of Brazilian Passiflora Seed Oils," Journal of Food Science, vol. 80, No. 12, pp. C2647-C2654, 2015.

Embree, "The Separation of Natural Components of Fats and Oils by Molecular Distallation," Chemical Reviews, vol. 29, No. 2, pp. 317-332, 1941.

International Search Report and Written Opinion issued in corresponding international application No. PCT/EP2014/070463 dated Dec. 9, 2014.

Liu et al., "Optimization of process parameters for supercritical carbon dioxide extraction of Passiflora seed oil by response surface methodology," The Journal of Supercritical Fluids, vol. 48, No. 9, pp. 9-14, 2009.

Liu et al., "Physical and chemical analysis of Passiflora seeds and seed oil from China," International Journal of Food Sciences and Nutrition, vol. 59, No. 7-8, 2008, pp. 706-715.

Malacrida et al., "Yellow Passion Fruit Seed Oil (*Passiflora edulis* f. *flavicarpa*): Physical and Chemical Characteristics," Brazilian Archives of Biology and Technology, vol. 55, No. 1, 2012, pp. 127-134.

* cited by examiner

METHODS OF TREATMENT USING A LIPID EXTRACT OF *PASSIFLORA* SEEDS CONCENTRATED IN ITS UNSAPONIFIABLE FRACTION

The invention relates to a lipid extract from *Passiflora* seeds, *Passiflora incarnata* and *Passiflora edulis* and preferably *Passiflora edulis*, and to a cosmetic, dermatological or nutraceutical composition comprising a suitable excipient and said lipid extract of seeds from *Passiflora incarnata* and *Passiflora edulis*. The inventors have surprisingly discovered that lipid extracts from *Passiflora* seeds and preferably those of *Passiflora edulis* have cosmetic, dermatological or nutraceutical properties of interest.

A further subject of the invention is a process to extract a lipid extract from *Passiflora* seeds and the extract able to be obtained using said process. The invention also concerns said composition or said extract for use in the prevention or treatment of disorders or pathologies of the skin, mucosae or skin appendages. Finally the invention is directed towards a method for cosmetic care of the skin, skin appendages or mucosae with a view to improving the condition or appearance thereof entailing the administration of said composition or said extract.

Passiflora

The *Passiflora* family is formed of about 500 species. The species are often distributed in warm temperate and tropical regions and in particular throughout the American continent, but are rather rarely found in Asia, Australia and tropical Africa.

Botanics

The plants are in the form of shrubs or vines. The leaves are alternate, at times simple, lobed or palmate. The flowers can reach 9 cm in diameter and are bisexual or unisexual and regular. They are white and purple and have filiform petaloid appendages with filaments symbolizing Christ's crown of thorns. The fruit 4 to 5 cm in length is oval and often of yellow to orange colour.

The most widespread species are *P. incarnata* and *P. edulis* in particular.

Phytochemical Aspects

*P. incarnata*: the major constituents are represented by the flavonoid family which are found in large amounts in the leaves. They have high isovitexin content. They also contain a small amount of simple indole alkaloids (harmane, harmine . . . ), sugars such as raffinose, sucrose, fructose, glucose, as well as essential oils and maltol described as being the molecule responsible for the sedative and anticonvulsive effects attributed to this plant.

*P. edulis*: from a methanol extract of dried leaves a specific compound has been identified: passiflorine—cyclopropane triterpene glycoside (E. Bombardelli et al., 1975). It contains isoorientin, a flavonoid which is not found in *P. incarnata* and traces of essential oil and and alkaloids identical to *P. incarnata*. The fruit pulp contains flavonoids, schaftoside, isoschaftoside, isoorientin, orientin, isovitexin, derivatives of luteolin (M. L. Zeraik, J. H. Yariwake—2010), ascorbic acid (about 60 mg/100 g). The pulp also contains glycosylated cyanogenic derivatives: prunasin, sambunigrin and amygdalin, and two more recently identified mandelonitrile β-rutinosides (D. Chassagne and J. Crouzet, 1998; D. S. Seigler, 2002).

Toxicology

Cyanogenic constituents are chiefly contained in the above-ground parts of different *Passiflora* varieties.

Seed Characteristics

The seeds account for 6 to 12% of the fruit of *P. Edulis* and contain:
  polyphenols including Piceatannol (structure close to resveratrol) and its dimer scirpusin B (S. Sano; K. Sugiyama; T. Ito, 2011), substances having vasorelaxing and antioxidant effects.
  oil, 18% via solvent containing phytosterols (0.2% including campesterol, stigmasterol, sitosterol, avenasterol); 60 to 73% linoleic acid (omega 6), 14% to 20% oleic acid and 465 ppm tocopherols (G. Piombo, N. Barouh et al, 2006; R. de V. V. Lopes et al.).
  Sugars and proteins

PRIOR ART

Food Use

The fruit appears to have been eaten since prehistoric times. In Peru in the $XVI^{th}$ century the magnificent *Passiflora* flowers were already considered to be a remedy and numerous *Passiflora* species are still used in numerous countries for common therapeutic applications.

Medical Use

*Passiflora* (often the above-ground parts and sometimes the fruit) are often used throughout the world as anxiolytic, sedative, diuretic and analgesic (all descriptions in "*Passiflora*: review update. K. Dhawan, S. Dhawan, A. Sharma, 2004"). Maltol and some of the derivatives thereof are said to be responsible for the sedative effect.

This action is reported to be more constant and more significant for *P. incarnata*. Extracts of *P. incarnata* are said to be capable of reversing morphine addiction. Anti-inflammatory effects have also been evidenced with extracts of *P. edulis* leaves.

The different families of polyphenols most probably make a major contribution to the antioxidant and protein antiglycation properties (M. Rudnicki, 2007) of the above-ground parts of *P. edulis*.

An anti-hypotensive effect of a methanol extract from the fruit rind of *P. edulis* and a cholesterol-lowering effect of an extract of delipidated seeds rich in fibre have also been evidenced. Anti-tumoral effect of fruit decoction via inhibition of matrix metalloproteinases (MMP2 and MMP9) involved in tumour invasion, metastases and angiogenesis.

Dermo-Cosmetic Use

Leaves of *P. foetida* used in Brazil to treat inflammatory skin diseases. In Mauritius and Rodrigues decoctions of the leaves of *P. suberosa* are used as a bath to treat skin diseases.

DESCRIPTION OF THE INVENTION

Figure 1A:
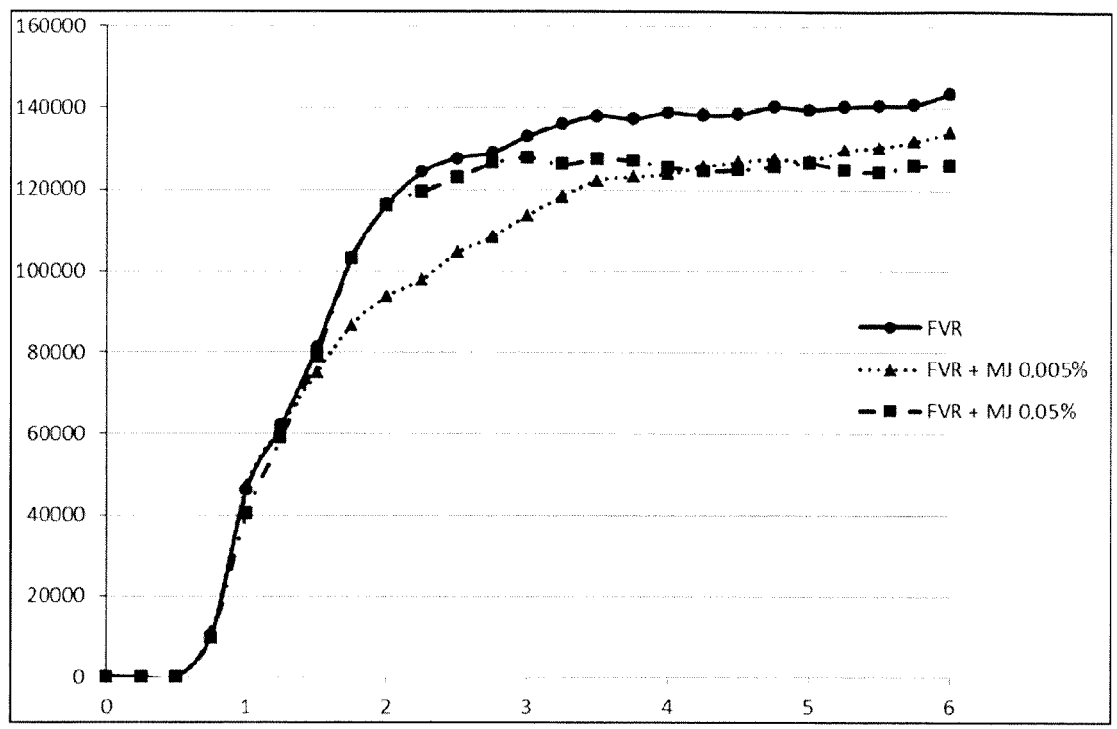
FIG. 1A shows contractile forces developed by red stretch mark fibroblasts (FVR) in the presence or absence of *Passiflora* concentrate (MJ) in a dermal equivalent tensioned in the GlaSbox® system (details of initial 6 hours).

The Applicant has discovered that the lipid extracts of the seeds of *Passiflora incarnata* and/or *edulis* exhibit cosmetic and dermatological properties that have never been described up until now. In particular, it is the first time that such *Passiflora* lipid extracts are used as such for their specific properties.

The subject of the invention is a composition comprising a lipid extract of *Passiflora* seeds optionally in association with a suitable excipient. The composition is advantageously cosmetic, pharmaceutical, dermatological, nutraceutical. Said composition is preferably formulated for administration via oral or external topical route.

The subject of the invention concerns a lipid extract of *Passiflora* seeds, *Passiflora incarnata* and/or *Passiflora edulis*, preferably *P. edulis*, characterized in that said lipid extract is an oil of *Passiflora* seeds concentrated in its unsaponifiable fraction containing 3% to 100% by weight, advantageously 4% to 100% by weight of unsaponifiables relative to the total weight of the extract.

The oil of *Passiflora* seeds concentrated in its unsaponifiable fraction contains the fatty acids of the original oil, and the fatty acid distribution of the concentrated *Passiflora* oil is identical to that of the *Passiflora* oil before concentration. Similarly, the unsaponifiable compounds and their respective distribution are identical in the starting oil and concentrated oil. On the other hand, the oil is concentrated in its unsaponifiable fraction, in particular it contains more than 3% by weight of unsaponifiables relative to the total weight of the oil, advantageously more than 4% by weight of unsaponifiables, further advantageously more than 4.5% by weight of unsaponifiables.

The oil of *Passiflora* seeds concentrated in its unsaponifiable fraction advantageously comprises fatty acids having 12 to 22, more advantageously 14 to 20 carbon atoms. These fatty acids may be saturated, mono-unsaturated or polyunsaturated.

One example of the characteristics of the crude oil of *Passiflora edulis* is given in following Table 1:

TABLE 1

Example of characteristics of crude *Passiflora* oil
Fatty fraction (wt. % relative to total oil weight)

| | |
|---|---|
| C14 (myristic acid) | ≤1.0 |
| C16 (palmitic acid) | 5.0-15.0 |
| C16' (5-hexadecenoic acid) | ≤1.0 |
| C18 (stearic acid) | ≤5.0 |
| C18' (oleic acid) | 10.0-20.0 |
| C18'' linoleic acid) | 60.0-80.0 |
| C18''' (α-linolenic acid) | <1.0 |
| C20 (arachidic acid) | ≤1.0 |
| C20' (eicasenoic acid) | ≤1.0 |
| C22 (behenic acid) | ≤1.0 |
| Tocopherol content (g/100 g) | 0.001-0.5 |
| Tocotrienol content (g/100 g) | 0.01-1.0 |
| Sterol content (g/100 g) | 0.1-2.0 |
| Squalene content (g/100 g) | 0.05-1.0 |
| Total unsaponifiable content (g/100 g) | 0.3-2.0 |

The unsaponifiable fraction is advantageously mostly composed of tocopherols, tocotrienols and sterols. Squalenes are also found.

In the unsaponifiable fraction the tocopherol content advantageously varies between 0.1 and 3 weight %, more advantageously between 0.5 and 3 weight %, further advantageously between 1 and 3 weight % tocopherols relative to the total weight of the unsaponifiable fraction. Among the tocopherols, α-tocopherol, β-tocopherol, δ-tocopherol and γ-tocopherol are advantageously found. These tocopherols advantageously account for 60 to 100 weight %, more advantageously 80 to 100 weight % of total tocopherol weight.

In the unsaponifiable fraction, the tocotrienol content advantageously varies between 5 and 25 weight %, more advantageously between 8 and 25 weight %, further advantageously between 10 and 20 weight % tocotrienols relative to the total weight of the unsaponifiable fraction. Among the tocotrienols, α-tocotrienol, β-tocotrienol, δ-tocotrienol are advantageously found. These tocotrienols advantageously form 60 to 100 weight %, more advantageously 80 to 100 weight % of total tocotrienol weight.

In the unsaponifiable fraction, the sterol content advantageously varies between 30 and 60 weight %, more advantageously between 35 and 55 weight %, further advantageously between 40 and 50 weight % of sterols relative to the total weight of the unsaponifiable fraction. Among the sterols, campesterol, stigmasterol, β-sitosterol and Δ7-stigmasterol are advantageously found. These sterols advantageously form 60 to 100 weight %, more advantageously 70 to 90 weight % of the total weight of the unsaponifiable fraction.

In the unsaponifiable fraction, the squalene content advantageously varies between 10 and 35 weight %, more advantageously 15 to 30 weight %, further advantageously between 15 and 25 weight % squalene relative to the total weight of the unsaponifiable fraction.

The unsaponifiable fraction therefore advantageously comprises tocopherols, tocotrienols, sterols and squalenes, preferably in the previously specified content. The unsaponifiable fraction may also comprise other non-identified unsaponifiables. Advantageously the content of non-identified unsaponifiables is less than 30 weight % relative to the total weight of the unsaponifiable fraction, more advantageously 0 to 25 weight %.

According to a first variant of the invention, the lipid extract is an oil of *Passiflora* seeds concentrated in its unsaponifiable fraction. It advantageously comprises 3 to 15 weight % of unsaponifiables relative to the total weight of the oil. It advantageously has the following specifications:

TABLE 2

Characteristics of concentrated *Passiflora* oil
Fatty fraction (wt. % relative to total oil weight)

| | |
|---|---|
| C14 (myristic acid) | ≤1.0 |
| C16 (palmitic acid) | 5.0-15.0 |
| C16' (5-hexadecenoic acid) | ≤1.0 |
| C18 (stearic acid) | ≤5.0 |
| C18' (oleic acid) | 10.0-20.0 |
| C18'' (linoleic acid) | 60.0-80.0 |
| C18''' (α-linolenic acid) | <1.0 |
| C20 (arachidic acid) | ≤1.0 |
| C20' (eicasenoic acid) | ≤1.0 |
| C22 (behenic acid) | ≤1.0 |
| Total unsaponifiable content (g/100 g) | 3.0-15.0 |

The unsaponifiable fraction is such as previously described.

According to a second variant of the invention, the lipid extract is the unsaponifiable fraction. This unsaponifiable fraction is such as previously described.

The lipid extract is advantageously obtained using a process comprising the following successive steps:
  a) molecular distillation of crude or refined *Passiflora* oil;
  b) optionally, extraction of the unsaponifiable;
  c) recovery of the oil concentrated in unsaponifiable obtained after step a) or of the unsaponifiable obtained after step b).

If it is desired to recover the oil rich in unsaponifiable, step b) is not carried out.

If it is desired to recover the unsaponifiable fraction, step b) is carried out. This step b) advantageously comprises the following successive steps:

i. saponification of the *Passiflora* oil concentrated in its unsaponifiable fraction obtained after step a);
ii. followed by extraction of the unsaponifiable using a suitable solvent.

This process is described further on.

A further subject of the invention is a process to prepare an extract of the invention comprising the following successive steps:

a) molecular distillation of crude or refined *Passiflora* oil;
b) optionally, extraction of the unsaponifiable;
c) recovery of the oil concentrated in unsaponifiable obtained after step a) or of the unsaponifiable obtained after step b).

Starting from *Passiflora* seeds, the process comprises a first extraction step of the oil using technologies known to person skilled in the art e.g. pressing, solvent extraction, under supercritical pressure and more particularly by pressing or under supercritical pressure and preferably by pressing. The oil may or may not be refined using technologies known to skilled persons, and is preferably non-refined. This oil is then subjected to molecular distillation to yield oil concentrated in its unsaponifiable fraction (or concentrate).

Oils can be extracted using several methods:
physical extraction such as cold pressing on a mechanical press, pressing on a twin-screw extruder;
chemical extraction using organic solvents (aliphatic alkanes, alcohols, chlorinated solvents, fluorinated solvents);
extraction in supercritical medium using carbon dioxide for example alone and/or with co-solvents.

For the extraction of crude *Passiflora* oil, priority is given to cold pressing on a mechanical press.

The crude *Passiflora* oil can be refined using processes known to skilled persons such as physical refining (degumming with water, deacidification by high temperature deodorization) and chemical refining (degumming with water or acid treatment to remove phospholipids, neutralization of free fatty acids using a basic solution, decolourization, winterization and deodorization).

The previously obtained crude *Passiflora* crude oil is advantageously concentrated in its unsaponifiable fraction via a molecular distillation process.

The unsaponifiable is the fraction of fat which, after extended action of an alkaline base, remains water-insoluble and can be extracted with an organic solvent. Five major groups of substances are contained in most unsaponifiables of vegetable oils: saturated or unsaturated hydrocarbons, aliphatic or terpene alcohols, sterols, tocopherols, tocotrienols, carotenoid pigments and xanthophylls.

This molecular distillation step is preferably conducted using a device selected from among molecular distillation units of centrifugal type and molecular devices of scraped film type.

Molecular distillation units of centrifugal type are known to persons skilled in the art. For example application EP 493 144 describes a molecular distillation unit of this type. In general, the product to be distilled is spread in a thin layer over the heated surface (hot surface) of a conical rotor rotating at high speed. The distillation chamber is placed under a vacuum. Under these conditions, evaporation and not boiling of the oil constituents such as unsaponifiables takes place on the hot surface, the advantage being that the oil and its constituents, in particular the unsaponifiables (these products considered to be fragile) are not deteriorated by evaporation.

Molecular distillation units of scraped film type are also known to skilled persons. In general, they comprise a distillation chamber equipped with a rotating scraper allowing continuous spreading of the products to be distilled on the evaporation surface (hot surface). Product vapours are condensed via a chilled finger placed in the centre of the distillation chamber. The peripheral feed and vacuum systems are very close to those of a centrifugal distillation unit (feed pumps, vacuum oil diffusion vane pumps, etc.). Recovery of residues and distillates in glass flasks is obtained by gravitational flow.

After the fractionating step the distilled fraction rich in unsaponifiables advantageously represents 3 to 15 weight % of the starting oil, and the distilled fraction rich in triglycerides advantageously represents 85 to 97 weight % of the starting oil.

Additionally, it has been verified that this process does not lead to any chemical change or deterioration of the compounds of the unsaponifiable and that the highly unsaturated fractions are preserved. As a result, the fatty acid distribution of the concentrated *Passiflora* oil is identical to that of the *Passiflora* oil before concentration.

After this molecular distillation step, the product obtained can optionally be deodorized and/or decolourized using processes known to persons skilled in the art.

The *Passiflora* oil concentrated in its unsaponifiable fraction thus obtained has the characteristics described in the foregoing.

If it is desired to recover the oil enriched with unsaponifiable, step b) is not performed.

If it is desired to recover the unsaponifiable fraction, step b) is carried out. This step advantageously comprises the following successive steps:
i. saponification of the *Passiflora* oil concentrated in its unsaponifiable fraction, obtained after step a);
ii. followed by extraction of the unsaponifiable using a suitable solvent.

The unsaponifiable of *Passiflora* oil can be obtained using methods known to skilled persons. For example it can be obtained by saponifying the *Passiflora* oil concentrated in its unsaponifiable fraction, then extracting this unsaponifiable using a suitable solvent. This extract is then washed until complete removal of the soaps and the solvent evaporated. Finally the unsaponifiable is advantageously subjected to deodorization with water vapour and nitrogen stripping to remove all traces of solvent.

The unsaponifiable of *Passiflora* oil thus obtained advantageously has the characteristics described in the foregoing.

In the invention, the lipid extract of *Passiflora* seeds is itself selected from the group formed by oil concentrated in its unsaponifiable fraction, an unsaponifiable fraction, the unsaponifiable fraction having the previously given specifications.

A further subject of the invention is a composition comprising as active ingredient a lipid extract of *Passiflora* seeds according to the invention and a suitable excipient.

The composition advantageously comprises 0.01 to 20 weight % of said lipid extract relative to the total weight of the composition.

The extract is advantageously used as active agent in a composition such as a cosmetic, dermatological or pharmaceutical composition which may comprise one or more suitable excipients. The composition may additionally comprise at least one other active compound in addition to the lipid extract of *Passiflora*. This other compound can be selected from among all the compounds and the functional equivalents thereof set forth above.

This other compound can in particular be selected from among active agents conventionally used in dermatology or cosmetics such as emollients, hydrating agents, keratin synthesis activators, keratin regulators, keratolytics, skin barrier restructuring agents (activators of skin lipid synthesis), PPAR agonists (Peroxysome Proliferator Activated Receptor), RXR or LXR agonists, sebum regulators, anti-irritant agents, soothing agents, anti-inflammatory agents, antioxidant agents and anti-aging agents, depigmenting or hypo/depigmenting agents, pigmenting agents, lipolytic agents or lipogenesis inhibitors, or anti-cellulite or slimming agents, mineral or organic sun filters and sunscreens, anti-fungal compounds, preserving agents, anti-bacterial agents, pre- and probiotics, antibiotics, immuno-modulators.

More particularly, the healing and/or restructuring agents of the skin barrier able to be used in association are advantageously panthenol (vitamin B5), arabinogalactan, zinc oxide, ceramides, cholesterol, squalane and phospholipids.

Sebum regulators able to be used in association are advantageously selected from the group formed by 5-alpha-reductase inhibitors. Zinc (and zinc derivatives such as the gluconate and salicylate salts thereof and pyroglutamic acid) and spironolactone, also have sebum suppressive action. Other sebum regulators or lipid origin acting on sebum quality such as linoleic acid are also of interest.

The anti-inflammatory and/or anti-irritant and/or soothing agent may be arabinogalactan.

The sun protection active ingredients able to be used in association are advantageously UVB and/or UVA sun filters and sunscreens, such as mineral and/or organic screens or filters known to persons skilled in the art who are able to adapt the choice and concentration thereof as a function of the desired level of protection.

The preserving agents able to be used in association are for example those generally used in cosmetics, molecules having antibacterial action (pseudo-preserving agents) such as caprylic derivatives e.g. caprylolyl glycine and glyceryl caprylate; hexanediol, sodium levulinate, and derivatives of zinc and copper (gluconate and PCA).

Among the active ingredients recommended in association with the extract of the invention, mention can be made of plant extracts and in particular:
- vegetable oils such as soybean oil and/or rapeseed oil, avocado oil (WO2004/012496, WO2004/012752, WO2004/016106, WO2007/057439), lupin oil and advantageously sweet white lupin oil (WO98/47479), or a mixture of these oils;
- the oleodistillate or concentrates of vegetable or animal oil, in particular sunflower oil, more particularly concentrates of linoleic sunflower such as sunflower oil rich in unsaponifiables (Soline®—WO2001/21150), marketed by Laboratoires Expanscience, oils rich in unsaponifiables of avocado, rapeseed, corn oil type notably used for their hydrating and/or emollient, healing and/or restructuring action on the skin barrier, anti-inflammatory and/or anti-irritant and/or soothing action;
- The unsaponifiables of plants or vegetable oil, advantageously avocado furans (Avocadofurane®) able to be obtained using the method described in international application WO 01/21605, the unsaponifiables of avocado and/or soybean more particularly a mixture of avocado furan unsaponifiables and soybean unsaponifiables, advantageously in a respective ratio of about 1:3-2:3 (such as Piascledine®), the unsaponifiables of soybean (such as obtained using the method described in international application WO 01/51596), sterol unsaponifiables (typically unsaponifiables having a content of sterols, methylsterols and triterpene alcohols of between 20 and 95 weight %, preferably 45-65 weight % relative to the total weight of the unsaponifiable), phytosterols, sterol esters and vitamin derivatives used in particular for their healing and/or restructuring action on the skin barrier and anti-ageing and anti-inflammatory action;
- The peptides or complexes of plant amino acids in particular of avocado (such as those described in international application WO2005/105123), lupin peptides (such as those described in international application WO2005/102259), quinoa peptides (such as those described in international application WO2008/080974), maca peptides (such as those described in international application WO2004/112742), soybean peptides whether or not fermented, rice peptides (such as those described in international application WO2008/009709), useful in particular for their hydrating and/or emollient action (avocado), keratin-regulating action (lupin, quinoa), healing and/or restructuring action on the skin barrier (maca, quinoa, soy), anti-inflammatory and/or anti-irritant and/or soothing action (lupin, quinoa), antioxidant (avocado), anti-aging (lupin, maca), pigmenting (rice), schizandra peptides (such as those described in patent application FR 0955344), extract of *Acacia macrostachya* seeds (such as the extract described in application WO 2011/064402), extract of *Vigna unguiculata* seeds (such as the extract described in application WO 2011/064401); the peptide and osidic extracts of *Passiflora* seeds (such as described in patent application FR 1262234)
- Plant sugars in particular avocado sugars (such as those described in application WO2005/115421), particularly useful for their keratin-regulating, skin barrier healing and/or restructuring property, anti-inflammatory and/or anti-irritant and/or soothing action;
- Butyl avocadate (5 alpha Avocuta®), inhibitor of 5-alpha reductase (WO 01/52837 and WO 02/06205) and typically a regulator of seborrhoea secretion that is in increased in acne and dandruff;
- Extracts rich in polyphenols, and more particularly extracts of avocado fruit (such as those described in application FR 1 061 055), extracts of maca leaves (such as those described in application FR 1 061 047), and extracts of above-ground parts of *Gynandropsis gynandra* (such as those described in application FR 1 061 051);
- Lupeol (FR 2 8 22 821, FR 2 857 596) particularly useful to promote healing;
- Cupuacu butter particularly appreciated for its hydrating properties.

Among the active ingredients recommended in association with the extract of the invention mention can be made of oxazolines, in particular those selected from the group formed by 2-undecyl-4-hydroxymethyl-4-methyl-1,3-oxazoline, 2-undecyl-4,4-dimethyl-1,3-oxazoline, (E)-4,4-dimethyl-2-heptadec-8-enyl-1,3-oxazoline, 4-hydroxymethyl-4-methyl-2-heptadecyl-1,3-oxazoline, (E)-4-hydroxymethyl-4-methyl-2-heptadec-8-enyl-1,3-oxazoline, 2-undecyl-4-ethyl-4-hydroxymethyl-1,3-oxazoline (preferably 2-undecyl-4,4-dimethyl-1,3-oxazoline, called OX-100 or Cycloceramide®; WO2004050052, WO2004050079 and WO2004112741). They are particularly useful for their anti-inflammatory and/or anti-irritant and/or soothing, antioxidant, depigmenting, immune-modulating action.

All these associations comprise at least one other active compound in addition to the extract of *Passiflora* seeds and may comprise two, three, four or more active compounds such as previously described.

The composition of the invention can be formulated in the form of different preparations adapted for topical administration, oral, rectal, vaginal, nasal, aural or bronchial administration, and parenteral administration. Advantageously the composition of the invention is formulated in the form of a preparation adapted for topical administration or oral administration.

According to a first variant the different preparations are adapted for topical administration and particularly include creams, emulsions, milks, ointments, lotions, oils, aqueous, aqueous-alcoholic or glycolic solutions, powders, patches, sprays, shampoos, varnishes or any other product for external application.

The composition comprising an extract of *Passiflora* seeds having the indicated specifications is particularly intended for cosmetic, pharmaceutical, dermatological, nutraceutical use.

For cosmetic, pharmaceutical or dermatological use, the composition is advantageously formulated in the form of a preparation adapted for topical administration. The composition comprising a lipid extract of *Passiflora* seeds, itself selected from the group formed by oil concentrated in its unsaponifiable fraction, an unsaponifiable, is particularly intended for cosmetic, pharmaceutical or dermatological use.

For nutrient or cosmetic food use ("cosmet-food"), the composition is advantageously formulated in the form of a preparation adapted for oral administration.

A further subject of the invention is an extract of the invention or a composition of the invention for use as or in a dermatological, pharmaceutical composition, or as or in a functional food.

A functional food is a conventional food or which has the appearance thereof and is part of a normal diet and has the characteristic of providing beneficial physiological effects exceeding its usual nutritional functions or of reducing the risk of chronic diseases.

It has been shown that the extract of the invention, and in particular a *Passiflore edulis* oil concentrated in its unsaponifiable fraction:
  contributes towards protecting the dermis against oxidative damage;
  increases the biosynthesis of hyaluronic acid and hence promotes hydration of the dermis and dermal elasticity;
  contributes towards increasing fibrillogenesis and remodelling of the dermal extracellular matrix to allow better cohesion and elasticity of the dermis;
  increases the proliferation of normal human fibroblasts;
  reduces contractile forces generated by the fibroblasts of red stretch marks;
  promotes adipocyte lipolysis;
  represses the expression of genes involved in melanogenesis.

Advantageously the composition or extract of the present invention is used for the prevention and/or treatment of disorders or pathologies of the skin and/or mucosae and/or skin appendages. In particular the composition or extract of the invention is used to stimulate, restore or regulate the metabolism of skin and mucosae cells and/or to prevent and/or treat disorders related to the dermal tissue.

In particular the extract of the invention can be used for one or more of the following indications:
  as anti-ageing agent;
  as healing agent;
  to prevent deterioration of and/or to maintain homeostasis of the skin or mucosae;
  as antioxidant agent;
  as anti-inflammatory agent;
  as slimming and/or anti-cellulite agent;
  to prevent or treat skin stretch marks;
  as depigmenting agent.

More particularly the composition or extract of the invention can be used to prevent or delay premature, in particular photo-induced skin ageing. They are therefore useful in a cream or formulation intended to prevent, reduce and/or treat wrinkles, lines or deterioration of the microrelief.

Through its action on the proliferation of fibroblasts and particularly on collagen, the composition or extract of the invention can be used to reinforce the mechanical properties of the skin and mucosae, in particular to combat withered, flabby, sagging and/or thinned skin, and/or to reinforce and/or restore skin elasticity or firmness.

The composition or extract of the invention can also be used for the prevention and/or treatment of deteriorated adipose tissue.

In particular the composition or extract of the invention is intended for the prevention and/or treatment of allergic, inflammatory, irritant reactions or pathologies, or disorders of the barrier or homeostasis of the skin, of skin appendages (hair and nails) and/or immature, normal or mature/aged mucosae (gums, periodontium, genital mucosae).

The composition or extract of the invention can also be used to promote healing. The composition or extract of the invention can therefore be used in the prevention and/or treatment of pathologies or conditions selected from the group formed by surface scars, fragile lips and cheilitis, stretch marks, skin after stings and bites, skin abrasions, spots and/or skin scabs, and fragile and sensitive skin. Therefore the composition or extract of the invention is particularly adapted for the prevention or treatment of skin stretch marks.

By the expression "prevention of skin stretch marks" according to the present invention is meant action allowing the prevention or at least the reduced formation of stretch marks i.e. their length, width and/or depth as part of cosmetic or dermatological treatment by application of the composition before or during an event known to cause the onset of stretch marks such as pregnancy. By the expression "treatment of skin stretch marks" according to the present invention is meant action causing the regression i.e. to regress i.e. resorb already formed stretch marks i.e. their length, width and/or depth as part of cosmetic or dermatological treatment.

Therefore the composition used according to the invention can be applied to areas of the skin likely to form stretch marks, comprising stretch marks being formed or even comprising already formed stretch marks.

Advantageously, the composition or extract of the invention can be used to prevent and/or treat reactions, disorders or pathologies:
  of the skin, such as acne, rosacea or rosacea erythema, psoriasis, vascular disorders, diaper dermatitis, atopic dermatitis, eczema, contact dermatitis, irritant dermatitis, allergic dermatitis, seborrheic dermatitis (cradle cap), psoriasis, sensitive skin, reactive skin, dry skin (xerosis), dehydrated skin, skin with redness, skin erythema, aged or photo-aged skin, photosensitized skin, pigmented skin (melasma, post-inflammatory pigmentation . . . ), depigmented skin (vitiligo), skin with cellulitis, slackened skin, skin with stretch marks, dry patches, skin chapping, stings and bites, cracked skin in particular of the breasts, sunburn, inflammation due to all kinds of radiation, irritations due to agents e.g. chemical, physical (e.g. support wear for pregnant women), bacteriological, fungal or viral, parasitic (fleas, gale, ringworm, mites, dermatophytes), radiological or through inborn immune deficiency (antimicrobial peptides) or acquired (cellular, humoral, cytokines), and/or of mucosae such as gums and periodontium possibly exhibiting gingivitis (sensitive gums of newborns, hygiene problems due to smoking or other), periodontal disease, genital mucosae with possible irritation of external or internal male or female genital areas; and/or of skin appendages such as nails (brittle, fragile nails . . . ) and hair (alopecia, dandruff, hirsutism, seborrheic dermatitis, folliculitis) whether immature, normal or mature, particularly with scalp disorders such as androgenic, acute, localised, scarring, congenital, new-born occipital, areata alopecia due to chemotherapy/radiotherapy, or telogen effluvium, anagen effluvium, hair dystrophy, trichotillomania, ringworm or oily or dry dandruff.

The invention also concerns a method for cosmetic care of the skin and/or skin appendages and/or mucosae with a view to improving the condition and/or appearance thereof, advantageously with a view to improving, firmness, elasticity or tonicity of the skin comprising the administration via oral or topical route of an extract of the invention or a composition of the invention.

A further subject of the invention is a method for the cosmetic treatment of dry skin with feelings of tightness, comprising the administration via oral or topical route of an extract of the invention or a composition of the invention.

A further subject of the invention is a cosmetic treatment method to remodel the silhouette, limit "orange peel" effect comprising the administration via oral or topical route of an extract of the invention or a composition of the invention.

A final subject of the invention is a functional food comprising a lipid extract such as previously defined. The functional food can be selected from among:

1) Dairy products: such as cheese, butter, milk and other milk beverages, mixtures and spreads containing milk products, ice creams and yoghurts;
2) Fat-containing products such as margarines, spreads, mayonnaises, cooking fats, frying oils and vinaigrettes;
3) Cereal-containing products such as bread, pasta, whether these foods are prepared, baked in the oven or processed.
4) Confectionery such as chocolate, sweets, chewing gum, puddings, toppings, sorbets, icings and other garnishes;
5) Beverages whether or not alcoholic including sodas or other non-alcoholic beverages, fruit juices, dietary supplements, substitute meals in the form of drinks such as those sold by Boost™ and Ensure™ et;
6) Miscellaneous products such as eggs, processed foods such as soups, ready-made sauces for pasta, prepared meals and other like products.

The composition or extract of the present invention can be directly incorporated, without any modification, in foods, nutraceuticals, dietary products in particular high-protein products, beverages using techniques such as mixing, infusion, injection, blending, absorption, kneading and spraying.

The administration modes, dosages and optimal pharmaceutical forms of the compounds and compositions of the invention can be determined following criteria generally taken into account for pharmaceutical particularly dermatological treatment, or veterinary treatment, adapted to a patient or animal e.g. age or body weight of the patient or animal, seriousness of general condition, tolerance to treatment, ascertained side effects, type of skin.

BIBLIOGRAPHICAL REFERENCES

Georges PIOMBO et al, OCL vol. 13 no. 2-3 March-June 2006

Martina RUDNICKI et al., Food Chemistry 100 (2007) 719-724

David CHASSAGNE and Jean CROUZET, Phytochemistry, vol. 49, no. 3 pp 757-759, 1998

Ezio BOMBARDELLI et al. Phytochemistry, 1975, Vol. 14, pp 2661-2665

Shoko SANO et al. Agric. Food Chem., 2011, 59, 6209-6213

Kamaldeep DHAWAN et al. Journal of Ethnopharmacology 94 (2004) 1-23

Zerark et al. Microchemical Journal 96(2010), 86-91

R. de V. Vieira Lopes et al. Eur. J. Lipid. Sci. Technol. 2010, 112, 1253-1262

Seigler et al. Phytochemistry 60 (2012), 873-882

Example 1: Concentrate of the Invention

One example of a concentrate of the invention is a crude oil of *P. Edulis* concentrated in its unsaponifiable fraction. The extract is prepared by molecular distillation.

This extract has the following weight distribution:

TABLE 3

| Fatty fraction (wt. % relative to total oil weight) | |
|---|---|
| C14 | 0.1 |
| C16 | 13.3 |
| C16' | 0.4 |
| C18 | 2.5 |
| C18' | 15 |
| C18" | 67.5 |
| C18''' | 0.4 |
| C20 | 0.1 |
| C20' | 0.1 |
| C22 | 0 |
| C22' | 0 |
| Tocopherol content (g/100 g) | 0.09 |
| Tocotrienol content (g/100 g) | 0.57 |
| Sterol content (g/100 g) | 2.13 |
| Squalene content (g/100 g) | 0.87 |
| Total unsaponifiable content (g/100 g) | 4.7 |

Tocopherol; have the following weight distribution:

TABLE 4

| % α-tocopherol | 7.5 |
|---|---|
| % β-tocopherol | 3.5 |
| % δ-tocopherol | 17 |
| % γ-tocopherol | 72 |

Tocotrienols have the following weight distribution:

TABLE 5

| | |
|---|---|
| % α-tocotrienol | 2 |
| % δ-tocotrienol | 58 |
| % γ-tocotrienol | 40 |

Sterols have the following weight distribution:

TABLE 6

| | |
|---|---|
| % campesterol | 9.5 |
| % stigmasterol | 24 |
| % β-sitosterol | 33 |
| % Δ7-stigmasterol | 3.5 |
| % non-identified | 30 |

Example 2: Compositions for Application Via Topical Route

Several compositions for application via topical route are given below. The lipid extract of *Passiflora* seeds, itself selected from the group formed by oil concentrated in its unsaponifiable fraction and an unsaponifiable, can be incorporated in various cosmetic products such as cleansing water, oil-in-water emulsions, water-in-oil emulsions, oils, milks, lotions, shampoos, foaming and spray products, having compositions of which examples are given below.

Hydrating Cleansing Water:

| Raw material/Trade name or INCI name | % |
|---|---|
| PURIFIED WATER | QS to 100% |
| BIOSACCHARID GUM | From 1 to 5% |
| BUTYLENE GLYCOL | From 1 to 5% |
| HYALURONIC ACID | From 0 to 5% |
| PASSIFLORA CONCENTRATE | From 0.001 to 20% |
| PRESERVING AGENTS | From 0 to 1% |
| CITRIC ACID MONOHYDRATE | From 0 to 1% |
| TRIMETHAMINE | From 0 to 1% |

Cleansing Water, Sensitive Skin:

| Raw material/Trade name or INCI name | % |
|---|---|
| CAPRYLOYL GLYCINE | From 0 to 1% |
| SODIUM HYDROXIDE LYE | From 0 to 1% |
| SEQUESTERING AGENT | From 0 to 1% |
| BUTYLENE GLYCOL | From 1 to 5% |
| BETA CAROTENE | From 0 to 2% |
| PASSIFLORA CONCENTRATE | From 0.001 to 20% |
| PRESERVING AGENTS | From 0 to 1% |
| PEG-32 | From 1 to 5% |
| PEG-7 PALMCOCOATE | From 1 to 5% |
| ZINC GLUCONATE | From 0 to 1% |
| CITRIC ACID | From 0 to 1% |
| PURIFIED WATER | QS to 100% |
| PERFUME | From 0 to 1% |
| POLOXAMER 184 | From 1 to 5% |

Anti-Age Emulsion:

| Raw material/Trade name or INCI name | % |
|---|---|
| LIQUID ISOPARAFFIN | From 5 to 20% |
| ISOCETYL STEARATE | From 5 to 20% |
| AL—MG HYDROXYSTEARATE | From 5 to 20% |
| ABIL WE 09 | From 1 to 5% |
| GLYCEROL | From 1 to 5% |
| VASELINE OIL | From 1 to 5% |
| MICRONIZED ZINC OXIDE | From 1 to 5% |
| BUTYLENE GLYCOL | From 1 to 5% |
| RETINOL | From 0 to 1% |
| VITAMIN C | From 0 to 5% |
| PASSIFLORA CONCENTRATE | From 0.01 to 20% |
| ISONONYL ISONONANOATE | From 1 to 5% |
| BEESWAX | From 1 to 5% |
| SODIUM TARTRATE | From 1 to 5% |
| SODIUM CHLORIDE | From 0 to 5% |
| GLYCINE | From 1 to 5% |
| PRESERVING AGENTS | From 0 to 1% |
| CHOLESTEROL | From 0 to 1% |
| PHYTOSPHINGOSINE | From 0 to 1% |
| TARTARIC ACID | From 0 to 1% |
| PURIFIED WATER | QS to 100% |

Restructuring Emulsion:

| Raw material/Trade name or INCI name | % |
|---|---|
| HYDROGENATED POLYDECENE | From 5 to 20% |
| LAURYLGLUCOSIDE-GLYSTEARATE | From 1 to 5% |
| DICAPRYLYL CARBONATE | From 1 to 5% |
| GLYCEROL | From 5 to 20% |
| CARBOPOL | From 0 to 1% |
| XANTHAN GUM | From 0 to 1% |
| ASIATIC ACID | From 0 to 1% |
| VITAMIN B5 | From 0 to 5% |
| PASSIFLORA CONCENTRATE | From 0.01 to 20% |
| SODIUM HYDROXIDE LYE | From 0 to 1% |
| PRESERVING AGENTS | From 0 to 1% |
| CITRIC ACID | From 0 to 1% |
| PURIFIED WATER | QS to 100% |

Slimming Oil:

| Raw material/Trade name or INCI name | % |
|---|---|
| SOLUBILISING AGENT | From 0 to 1% |
| SWEET ALMOND OIL | From 5 to 20% |
| COCO CAPRYLATE/CAPRATE | QS to 100% |
| REFINED MACADAMIA OIL | From 5 to 20% |
| GLYCEROL CAPRYLO CAPRATE | From 5 to 20% |
| ALPHA BISABOLOL NAT | From 0 to 1% |
| ALPHA TOCOPHEROL | From 0 to 1% |
| IVY EXTRACT | From 0 to 5% |
| PASSIFLORA CONCENTRATE | From 0.01 to 20% |
| PRESERVING AGENT | From 0 to 1% |
| ESTER | From 0 to 1% |

Milk for Dry Skin, Atopic:

| Raw material/Trade name or INCI name | % |
|---|---|
| SWEET ALMOND OIL | From 1 to 5% |
| CORN OIL | From 1 to 5% |
| STEARIC ACID | From 1 to 5% |
| C16 C18 CETYL ALCOHOL | From 0 to 1% |
| ANTI-FOAMING AGENT 70414 | From 0 to 1% |
| LAURIC ALCOHOL 11OE | From 1 to 5% |
| PEG 300 MONOLAURATE | From 0 to 1% |
| GLYCEROL MONOLEATE | From 0 to 1% |
| GLYCEROL MONOSTEARATE | From 1 to 5% |
| VITAMIN B12 | From 0 to 5% |
| PASSIFLORA CONCENTRATE | From 0.1 to 120% |
| PRESERVING AGENTS | From 0 to 1% |
| CITRIC ACID | From 0 to 1% |

| Raw material/Trade name or INCI name | % |
|---|---|
| TRISODIUM CITRATE | From 0 to 1% |
| PURIFIED WATER | QS to 100% |
| PERFUME | From 0 to 1% |
| GROUNDNUT OIL | From 1 to 5% |
| HYDROGENATED PALMIST OIL | From 1 to 5% |

Foam:

| Raw material/Trade name or INCI name | % |
|---|---|
| PURIFIED WATER | QS to 100% |
| LAUROAMPHOACETATE | From 5 to 20% |
| COCOGLUCOSIDE | From 5 to 20% |
| SURFACTANT 1 | From 5 to 20% |
| SURFACTANT 2 | From 5 to 20% |
| PEG 6000 DISTEARATE | From 1 to 5% |
| PRESERVING AGENTS | From 1 to 5% |
| *PASSIFLORA* CONCENTRATE | From 0.001 to 12% |
| CAMOMILE EXTRACT | From 1 to 5% |
| CITRIC ACID MONOHYDRATE | From 0 to 1% |
| SEQUESTERING AGENT | From 0 to 1% |
| PERFUME | From 0 to 1% |
| SODIUM HYDROXIDE LYE | From 0 to 1% |

Soothing Spray:

| Raw material/Trade name or INCI name | % |
|---|---|
| PURIFIED WATER | QS to 100% |
| TRILAURETH-4 PHOSPHATE | From 1 to 5% |
| DICAPRYLYL CARBONATE | From 1 to 5% |
| BUTYLENE GLYCOL | From 1 to 5% |
| ERYTHRITYL ESTER | From 1 to 5% |
| FLUID VASELINE OIL | From 1 to 5% |
| SHEA BUTTER | From 0 to 1% |
| VEGETABLE OIL | From 0 to 1% |
| PRESERVING AGENTS | From 0 to 1% |
| LYCOPENE | From 0 to 5% |
| *PASSIFLORA* CONCENTRATE | From 0.01 to 20% |
| SODIUM HYDROXIDE LYE | From 0 to 1% |
| PERFUME | From 0 to 1% |
| XANTHAN GUM | From 0 to 1% |
| CARBOPOL | From 0 to 1% |
| SEQUESTERING AGENT | From 0 to 1% |
| CITRIC ACID | From 0 to 1% |

Purifying Cream Wash:

| Raw material/Trade name or INCI name | % |
|---|---|
| PURIFIED WATER | QS to 100% |
| ARLATONE | From 10 to 30% |
| COCOGLUCOSIDE | From 5 to 20% |
| HYDROXYPROPYL GUAR | From 1 to 5% |
| CAPRYLOYL GLYCINE | From 0 to 2% |
| PRESERVING AGENTS | From 0 to 2% |
| PERFUME | From 0 to 1% |
| CITRIC ACID | From 0 to 1% |
| ZINC PCA | From 0 to 1% |
| *PASSIFLORA* CONCENTRATE | From 0.001 to 20% |

Anti-Acne Emulsion:

| Raw material/Trade name or INCI name | % |
|---|---|
| PEG 40 STEARATE | From 1 to 5% |
| PEG 5 GLYCERYL STEAR | From 1 to 5% |
| CERESIN WAX | From 1 to 5% |
| GLYCEROL MONOSTEARATE | From 1 to 5% |
| SORBITAN STEARATE | From 0 to 2% |
| CETYL ALCOHOL | From 0 to 2% |
| DI-MALATE ALCOHOL | From 5 to 20% |
| VITAMIN E | From 0 to 1% |
| VITAMIN B3 | From 0 to 5% |
| LINOLEIC ACID | From 0 to 1% |
| *PASSIFLORA* CONCENTRATE | From 0.01 to 20% |
| BUTYLENE GLYCOL | From 1 to 5% |
| PIROCTOLAMINE | From 0 to 1% |
| PRESERVING AGENTS | From 0 to 1% |
| GLYCEROL | From 1 to 10% |
| XANTHAN GUM | From 0 to 1% |
| ZINC PCA | From 0 to 2% |
| RICE STARCH | From 1 to 5% |
| NYLON 6 | From 0 to 2% |
| POLYACRYLAMIDE GEL | From 1 to 5% |
| VITAMIN B6 | From 0 to 1% |
| PERFUME | From 0 to 1% |
| PURIFIED WATER | QS to 100% |

Redness Relief Emulsion:

| Raw material/Trade name or INCI name | % |
|---|---|
| PEG 40 STEARATE | From 1 to 5% |
| PEG 5 GLYCERYL STEAR | From 1 to 5% |
| CERESINE WAX | From 1 to 5% |
| GLYCEROL MONOSTEARATE | From 1 to 5% |
| SORBITAN STEARATE | From 0 to 2% |
| CETYL ALCOHOL | From 0 to 2% |
| DI-MALATE ALCOHOL | From 5 to 20% |
| ESCULOSIDE | From 0 to 2% |
| *SOPHORA JAPONICA* | From 0 to 5% |
| VITAMIN E | From 0 to 1% |
| *PASSIFLORA* CONCENTRATE | From 0.01 to 20% |
| BUTYLENE GLYCOL | From 1 to 5% |
| PIROCTOLAMINE | From 0 to 1% |
| PRESERVING AGENTS | From 0 to 1% |
| GLYCEROL | From 1 to 10% |
| XANTHAN GUM | From 0 to 1% |
| ZINC PCA | From 0 to 2% |
| RICE STARCH | From 1 to 5% |
| NYLON 6 | From 0 to 2% |
| POLYACRYLAMIDE GEL | From 1 to 5% |
| VITAMIN B6 | From 0 to 1% |
| PERFUME | From 0 to 1% |
| PURIFIED WATER | QS to 100% |

Reparative Care:

| Raw material/Trade name or INCI name | % |
|---|---|
| PEG 40 STEARATE | From 1 to 5% |
| PEG 5 GLYCERYL STEAR | From 1 to 5% |
| CERESIN WAX | From 1 to 5% |
| GLYCEROL MONOSTEARATE | From 1 to 5% |
| SORBITAN STEARATE | From 0 to 2% |
| CETYL ALCOHOL | Prom 0 to 2% |
| DI-MALATE ALCOHOL | From 5 to 20% |
| VITAMIN E | From 0 to 1% |
| COENZYME Q10 | From 0 to 2% |
| CERAMIDE | From 0 to 5% |
| *PASSIFLORA* CONCENTRATE | From 0.01 to 20% |
| BUTYLENE GLYCOL | From 1 to 5% |
| PIROCTOLAMINE | From 0 to 1% |
| PRESERVING AGENTS | From 0 to 1% |
| GLYCEROL | From 1 to 10% |
| XANTHAN GUM | From 0 to 1% |
| ZINC PCA | From 0 to 2% |
| RICE STARCH | From 1 to 5% |
| NYLON 6 | From 0 to 2% |
| POLYACRYLAMIDE GEL | From 1 to 5% |

-continued

| Raw material/Trade name or INCI name | % |
|---|---|
| VITAMIN B6 | From 0 to 1% |
| PERFUME | From 0 to 1% |
| PURIFIED WATER | QS to 100% |

Depigmenting Emulsion:

| Raw material/Trade name or INCI name | % |
|---|---|
| ISONONYL ISONONANOATE | From 1 to 10% |
| ISOCETYL STEARATE | From 1 to 10% |
| PEG 40 STEARATE | From 1 to 5% |
| PEG 5 GLYCERYL STEAR | From 1 to 5% |
| PRESERVING AGENTS | From 0 to 1% |
| C16 C18 CETYL ALCOHOL | From 0 to 2% |
| PPG/SMDI POLYMER | From 0 to 1% |
| SALICYLIC ACID | From 0 to 2% |
| SQUALANE GEL | From 0 to 2% |
| DIOCTYL ETHER | From 1 to 10% |
| DI-MALATE ALCOHOL | From 1 to 10% |
| SUNFLOWER EXTRACT | From 1 to 10% |
| TROMETHAMINE | From 1 to 5% |
| BUTYLENE GLYCOL | From 1 to 10% |
| TRISODIUM CITRATE | From 0 to 1% |
| SCLEROTIUM GUM | From 0 to 1% |
| RICE STARCH | From 1 to 10% |
| POLYACRYLAMIDE GEL | From 0 to 1% |
| VITAMIN C | From 0 to 2% |
| GLYCINE | From 0 to 2% |
| PERFUME | From 0 to 1% |
| VITAMIN E | From 0 to 2% |
| CITRIC ACID | From 0 to 1% |
| SEPIWHITE | From 0 to 2% |
| *PASSIFLORA* CONCENTRATE | From 0.01 to 20% |
| PURIFIED WATER | QS to 100% |

Anti-Bacterial Roll-on Stick:

| Raw material/Trade name or INCI name | % |
|---|---|
| PURIFIED WATER | QS to 100% |
| BUTYLENE GLYCOL | From 1 to 5% |
| BENZOYL PEROXIDE | From 0 to 2% |
| CAPRILOYL GLYCINE | From 0 to 5% |
| ZINC PCA | From 0 to 5% |
| *PASSIFLORA* CONCENTRATE | From 0.1 to 20% |
| CARBOMER | From 0 to 2% |
| PRESERVING AGENTS | From 0 to 1% |
| CITRIC ACID | From 0 to 1% |
| TROMETHAMINE | From 0 to 1% |

Exfoliating Care:

| Raw material/Trade name or INCI name | % |
|---|---|
| ARLATONE DUO | From 5 to 20% |
| EXFOLIATING AGENT | From 1 to 10% |
| SCLEROTIUM GUM | From 1 to 10% |
| PRESERVING AGENTS | From 0 to 1% |
| CAPRYLOYL GLYCINE | From 0 to 1% |
| SODIUM HYDROXIDE | From 0 to 1% |
| *PASSIFLORA* CONCENTRATE | From 0.01 to 20% |
| SEQUESTERING AGENT | From 0 to 1% |

-continued

| Raw material/Trade name or INCI name | % |
|---|---|
| CITRIC ACID | From 0 to 1% |
| PURIFIED WATER | QS to 100% |
| PERFUME | From 0 to 1% |

Keratinising Lotion:

| Raw material/Trade name or INCI name | % |
|---|---|
| CETYL ALCOHOL | From 1 to 5% |
| SILICONE 345 | From 1 to 5% |
| ANTI-OXIDANT | From 0 to 1% |
| PURIFIED WATER | QS to 100% |
| CETRIMONIUM CHLORIDE | From 0 to 5% |
| QUININE | From 0 to 5% |
| VITAMIN B5 | From 0 to 5% |
| *PASSIFLORA* CONCENTRATE | From 0.01 to 20% |
| HYDROLYSED WHEAT PROTEIN | From 0 to 1% |
| PRESERVING AGENT | From 0 to 2% |
| PERFUME | From 0 to 1% |
| pH ADJUSTER | From 0 to 1% |

Anti-Dandruff Shampoo:

| Raw material/Trade name or INCI name | % |
|---|---|
| PURIFIED WATER | QS to 100% |
| LAUROAMPHOACETATE | From 5 to 20% |
| COCOGLUCOSIDE | From 5 to 20% |
| PEG 6000 DISTEARATE | From 1 to 5% |
| PRESERVING AGENTS | From 0 to 2% |
| VITAMIN F | From 0 to 5% |
| PIROCTONE OLAMINE | From 0 to 2% |
| *PASSIFLORA* CONCENTRATE | From 0.01 to 20% |
| ZINC PYRITHIONE | From 0 to 1% |
| pH ADJUSTER | From 0 to 1% |
| SEQUESTERING AGENT | From 0 to 1% |
| PERFUME | From 0 to 1% |

Hair Conditioning Fluid:

| Raw material/Trade name or INCI name | % |
|---|---|
| CETEARYL ALCOHOL CETEARETH - 33 | From 1 to 5% |
| QUATERNIUM-82 | From 0 to 2% |
| PURIFIED WATER | QS to 100% |
| HYDROLYZED WHEAT PROTEIN | From 0 to 5% |
| PRESERVING AGENTS | From 0 to 2% |
| pH ADJUSTER | From 0 to 1% |
| PERFUME | From 0 to 1% |
| CYSTEINE | From 0 to 5% |
| *PASSIFLORA* CONCENTRATE | From 0.01 to 20% |

Fortifying Hair Lotion:

| Raw material/Trade name or INCI name | % |
|---|---|
| PURIFIED WATER | QS to 100% |
| METHYL PROPANEDIOL | From 5 to 20% |
| PRESERVING AGENT | From 0 to 2% |
| pH ADJUSTER | From 0 to 1% |
| PERFUME | From 0 to 1% |
| BIOTIN | From 0 to 5% |
| VITAMIN B9 | From 0 to 5% |
| *PASSIFLORA* CONCENTRATE | From 0.01 to 20% |
| BETA-SITOSTEROL | From 0 to 1% |
| ETHYLHEXYL COCOATE | From 0 to 5% |
| PEG-40 CASTOR OIL | From 0 to 5% |

Photoprotective Stick:

| Raw material/Trade name or INCI name | % |
|---|---|
| CASTOR OIL | QS to 100% |
| OLEIC ALCOHOL | From 10 to 20% |
| PALMIST OIL | From 10 to 20% |
| POLYGLYCERIN-3-BEEWAX | From 10 to 20% |
| CANDELILLA WAX | From 10 to 20% |
| HECTORITE | From 10 to 20% |
| TITANIUM DIOXIDE | From 0 to 5% |
| *PASSIFLORA* CONCENTRATE | From 0.01 to 20% |
| SHEA BUTTER | From 0 to 5% |
| VITAMIN E | From 0 to 1% |

Suncream Spf 50+:

| Raw material/Trade name or INCI name | % |
|---|---|
| PURIFIED WATER B4 | QS to 100% |
| TITANIUM OXIDE | From 10 to 20% |
| CYCLOPENTASILOXANE | From 5 to 15% |
| OCTYL PALMITATE | From 5 to 15% |
| C12-C15 ALKYL BENZOATE | From 5 to 10% |
| DECYL PENTANOATE | From 5 to 10% |
| ZINC OXIDE | From 5 to 10% |
| GLYCEROL | From 1 to 5% |
| PEG-45/DODECYL GLYCOL COPOLYMER | From 1 to 5% |
| *PASSIFLORA* CONCENTRATE | From 0.01 to 20% |
| SODIUM CHLORIDE | From 1 to 5% |
| DEXTRIN PALMITATE | From 1 to 2% |
| VITAMIN E | From 0 to 2% |
| PRESERVING AGENTS | From 0 to 2% |
| HYDROXYPROPYL GUAR | From 0 to 1% |
| *ALOE VERA* | From 0 to 1% |
| SODIUM HYDROXIDE LYE | From 0 to 1% |
| EDTA 2 Na | From 0 to 1% |
| ZINC GLUCONATE | From 0 to 1% |

Sun Spray Spf 50+:

| Raw material/Trade name or INCI name | % |
|---|---|
| GLYCEROL CAPRYOYL CAPRATE | From 5 to 20% |
| CYCLOPENTASILOXANE | From 10 to 20% |
| DICAPRYLYL CARBONATE | From 5 to 20% |
| TINOSORB S | From 1 to 10% |
| TITANIUM OXIDE 100 | From 10 to 20% |
| HECTORITE | From 0 to 5% |
| ALPHA TOCOPHEROL | From 0 to 2% |
| LAURYLGLUCOSIDE-GLYSTEARATE | From 0 to 10% |
| PURIFIED WATER B4 | QS to 100% |
| CITRIC ACID | From 0 to 2% |
| PENTYLENE GLYCOL | From 0 to 5% |
| GLYCEROL | From 0 to 5% |
| XANTHAN GUM | From 0 to 2% |
| *PASSIFLORA* CONCENTRATE | From 0.01 to 20% |
| *ALOE VERA* | From 0 to 1% |
| ZINC GLUCONATE | From 0 to 1% |
| PRESERVING AGENTS | From 0 to 2% |
| TINOSORB M | From 1 to 10% |

Varnish for Fragile Brittle Nails:

| Raw material/Trade name or INCI name | % |
|---|---|
| ACRYLATE COPOLYMER | From 15 to 30% |
| ETHANOL | QS to 100% |
| ACETONE | From 5 to 20% |
| *PASSIFLORA* CONCENTRATE | From 0.01 to 5% |

Example 3: Biological Activity Tests on the Extract of the Invention

The tested extract was the concentrate in Example 1. In the tests it will be called "*Passiflora* concentrate". Unless otherwise indicated, percentages are expressed by weight of concentrate relative to the total weight of the tested composition.

A. In Vitro Activity—Modulation of Gene Expression

Analysis of gene expression modulation by the oil concentrated in unsaponifiable fraction—called *Passiflora* concentrate in the remainder hereof—was performed on two different models: normal human fibroblasts and melanized reconstructed human epidermis.

1) Effect on Gene Expression in Normal Human Fibroblasts

The effects of *Passiflora* concentrate in normal human fibroblasts were measured on the expression of genes involved in dermal biology, remodelling of conjunctive tissue and ageing via qRT-PCR and TaqMan microfluidic cards.

a. Material and Methods

Normal human dermal fibroblasts were incubated 24 hours in the presence of 0.01% and 0.05% *Passiflora* concentrate. After incubation, the cells were lysed and total RNAs were extracted and assayed. The differences in gene expression were analysed using quantitative RT-PCR with TaqMan cards. Analysis of changes in expression and statistical analyses were performed using Data Assist software (Applied Biosystems).

b. Results

The *Passiflora* concentrate significantly modulated expression of the genes involved in the following functions (cf. Table 7):

TABLE 7

List of genes having significant variation in expression in the presence of *Passiflora* concentrate in normal human fibroblasts.

| | Concentrate 0.01% | | Concentrate 0.05% | |
|---|---|---|---|---|
| Gene name | RQ | value of p | RQ | value of p |
| hyaluronic acid synthase 2 | 2.6872 | 0.0276 | — | — |
| Fibrillin-1 | 2.3906 | 0.0047 | — | — |
| procollagen-lysine 2-oxoglutarate 5-dioxygenase 1 (Lysyl hydroxylase (LH1)) | 2.1811 | 0.0253 | — | — |
| NAD(H)dehydrogenase, quinone 1 | 2.1395 | 0.0405 | 2.1312 | 0.0153 |
| Fibromodulin | 2.078 | 0.0339 | — | — |
| alpha 1 subunit of collagen 1 (COL1A1) | 1.6491 | 0.0248 | 1.4726 | 0.0091 |
| Catalase | — | — | 1.9473 | 0.0216 |
| alpha 1 subunit of collagen 7 (COL7A1) | — | — | 1.6802 | 0.0137 |
| alpha 1 subunit of collagen 4 (COL4A1) | — | — | 1.5343 | 0.0359 |
| Mitochondrial peptide methionine sulfoxide reductase | — | — | 1.5218 | 0.0375 |
| Lumican | — | — | 1.4417 | 0.0441 |
| Glutathione synthetase | — | — | 1.4294 | 0.016 |
| Fibronectin | — | — | 1.401 | 0.0419 |
| Matrix metalloproteinase 3 (stromelysin 1) | — | — | 1.328 | 0.043 |

RQ = relative quantity of expression of the gene relative to non-treated control (RQ = 1)

1) Anti-Oxidant Response

The *Passiflora* concentrate induced expression of the antioxidant enzymes Mitochondrial peptide methionine sulfoxide reductase, NADH dehydrogenase, catalase (the activity of which is reduced throughout ageing) and glutathion synthetase which catalyses the synthesis of glutathion (antioxidant molecule). Therefore by increasing these genes the *Passiflora* concentrate contributes towards protecting the dermis against oxidative damage.

2) Homeostasis of the Extracellular Matrix

The *Passiflora* concentrate induced the expression of hyaluronan synthase 2, an enzyme involved in the synthesis of hyaluronic acid, a polysaccharide known for its capacity to retain water, to give support to tissue architecture and skin elasticity and to regulate cell migration. The *Passiflora* concentrate therefore increases the biosynthesis of hyaluronic acid and thereby promotes hydration and elasticity of the dermis.

The *Passiflora* concentrate induced the expression of genes encoding collagens of type 1, 4 and 7, fibrillin (a component of elastic fibres), lysyl hydroxylase 1 (enzyme involved in the formation of elastic fibres), fibromodulin and lumican (small proteoglycans which regulate the formation of fibrils), fibronectin and MMP3 (involved in the remodelling of the collagen network). Therefore the *Passiflora* concentrate contributes towards increasing fibrillogenesis and remodelling of the dermal extracellular matrix to allow better cohesion and elasticity of the dermis.

2) Effect on the Expression of Genes in Melanized Reconstructed Human Epidermis

The effects of the *Passiflora* concentrate on the expression of genes involved in pigmentation were evaluated in melanized reconstructed human epidermis using qRT-PCR with TaqMan microfluidic cards.

a. Material and Methods

Reconstructed epidermis samples containing primary human melanocytes (from a donor of dark phototype) were incubated 24 hours in the presence of 0.01% and 0.05% *Passiflora* concentrate. After incubation the tissues were lysed and total RNAs extracted and assayed, the differences in gene expression were analyzed by quantitative RT-PCR using TaqMan cards. Analysis of changes in expression and statistical analyses were performed using Data Assist software (Applied Biosystems).

b. Results

The *Passiflora* concentrate significantly repressed expression of the genes tyrosinase and MITF (Microphtalmia-associated transcription factor), both involved in melanogenesis (cf. Table 8). Tyrosinase is a key enzyme in the production of melanin by the melanocytes whilst MITF regulates melanocyte differentiation and transcription of enzymes involved in the melanogenesis process. These reductions in expression suggest depigmenting action of the *Passiflora* concentrate. In addition, the *Passiflora* concentrate reduced expression of NGF a nerve growth factor receptor, a neurotrophin particularly involved in neurogenic inflammation.

TABLE 8

List of genes with significant variation in expression in the presence of *Passiflora* concentrate in melanized reconstructed human epidermis.

| Gene name | *Passiflora* concentrate 0.01% | | *Passiflora* concentrate 0.04% | |
| --- | --- | --- | --- | --- |
| | RQ | Value of p | RQ | Value of p |
| Small prolin-rich protein 2A | — | — | 0.6922 | 0.0268 |
| Beta nerve growth factor | — | — | 0.4978 | 0.0231 |

TABLE 8-continued

List of genes with significant variation in expression in the presence of *Passiflora* concentrate in melanized reconstructed human epidermis.

| Gene name | *Passiflora* concentrate 0.01% | | *Passiflora* concentrate 0.04% | |
| --- | --- | --- | --- | --- |
| | RQ | Value of p | RQ | Value of p |
| Tyrosinase | 0.8088 | 0.0417 | — | — |
| Transcription factor associated with microphthalmia | 0.5867 | 0.0186 | — | — |

RQ = relative quantity of gene expression relative to non-treated control (RQ = 1)

B. Action on the Dermal Extracellular Matrix

Fibroblast screening having shown a potential effect of the *Passiflora* concentrate on homeostasis of the dermal matrix, we sought to confirm this potential by examining first the effect of the *Passiflora* concentrate on the proliferation of fibroblasts and on their ability to produce the majority components of the extracellular matrix. In addition a stretch mark fibroblast model was used to evaluate the relaxing effect of the *Passiflora* concentrate on the forces developed by these particular cells.

1. Effect on the Proliferation of Normal Human Fibroblasts a. Material and Methods Normal human dermal fibroblasts were incubated 72 hours in 1% FCS culture medium in the presence of 0.005% and 0.01% *Passiflora* concentrate or in 10% FCS culture medium (positive control). After incubation, cell proliferation was evaluated by BrdU assay using a chemiluminescence ELISA method. BrdU (5-bromo-2'-deoxyuridine) is an analogue of thymidine which, during the cell cycle, becomes incorporated in the DNA of proliferating cells.

b. Results

The *Passiflora* concentrate significantly increased the proliferation of normal human fibroblasts (Table 9).

TABLE 9

Proliferation of normal human fibroblasts, luminescence intensity proportional to the quantity of incorporated BrdU expressed as percentage increase relative to non-treated control

| | | Control (1% FCS) | Positive control (10% FCS) | *Passiflora* concentrate 0.005% | *Passiflora* concentrate 0.01% |
| --- | --- | --- | --- | --- | --- |
| Cell proliferation | Mean luminescence intensity | 1506398 | 23575410 | 2741224 | 2615640 |
| | Increase (%) | | +1465% *** | +82% ** | +74% ** |

** $p < 0.01$;
*** $p < 0.001$ - One-factor variance analysis followed by Dunnett test 2. Effect on the Expression of Dermal Matrix Components a. Material and Methods Normal human dermal fibroblasts were incubated for 24 hours in 1 FCS culture medium in the presence of 0.005% and 0.05% *Passiflora* concentrate or TGFβ1 at 5 ng/ml (standard). After incubation, the total RNAs were extracted, assayed and retro-transcribed. The gene expression of collagen I and elastin were analysed by real-time quantitative RT-PCR.

b. Results

The *Passiflora* concentrate significantly increased gene expression of collagen type I and elastin (Table 10), constituent and majority macromolecules of the extracellular dermal matrix.

TABLE 10

Gene expression (in relative quantity) of collagen I and elastin in normal human fibroblasts treated with *Passiflora* concentrate; percentage increase relative to non-treated control

|  | Collagen I (Relative Quantity) | | Elastin (Relative Quantity) | |
| --- | --- | --- | --- | --- |
| Control | 1.00 | | 1.00 | |
| Standard (TGFβ1) | 1.30 | +30% ns | 1.40 | +40% * |
| *Passiflora* concentrate 0.005% | 1.44 | +44% ** | 1.58 | +58% ** |
| *Passiflora* concentrate 0.05% | 1.87 | +87% *** | 1.92 | +92% *** |

\* $p < 0.05$;
\*\* $p < 0.01$;
\*\*\* $p < 0.001$ - One-factor variance analysis followed by Dunnett test

3. Relaxant Effect in Stretch Mark Fibroblast Model

The GlaSbox® system was used to evaluate the relaxing effect of the *Passiflora* concentrate on fibroblasts taken from a recent stretch mark (red).

The GlaSbox® system allows measurement of the contractile forces developed by fibroblasts within a dermal equivalent.

The fibroblasts from the red stretch mark develop greater contractile forces than the fibroblasts of healthy skin.

a. Material and Methods

Fibroblasts from healthy skin and fibroblasts from a red stretch mark taken after biopsy in one same patient were placed in culture. The dermal equivalents were prepared by mixing the fibroblasts (of healthy skin or red stretch mark) with a collagen solution. This mixture was poured into the rectangular wells of the GlasBox®. Medium containing or not containing 0.005% or 0.05% *Passiflora* concentrate was added. Two flexible silicon beams are immersed in each of the wells. The dermal equivalent therefore develops between two beams equipped with a strain gauge ("sensor"). Under the influence of the retraction force developed by the fibroblasts, the silicon beams become deformed; this translates as variation in the electrical resistance value of the strain gauge. This variation measured in real-time represents the force developed within the dermal equivalent. Isometric forces were measured for 24 hours.

b. Results

Figure 1B:
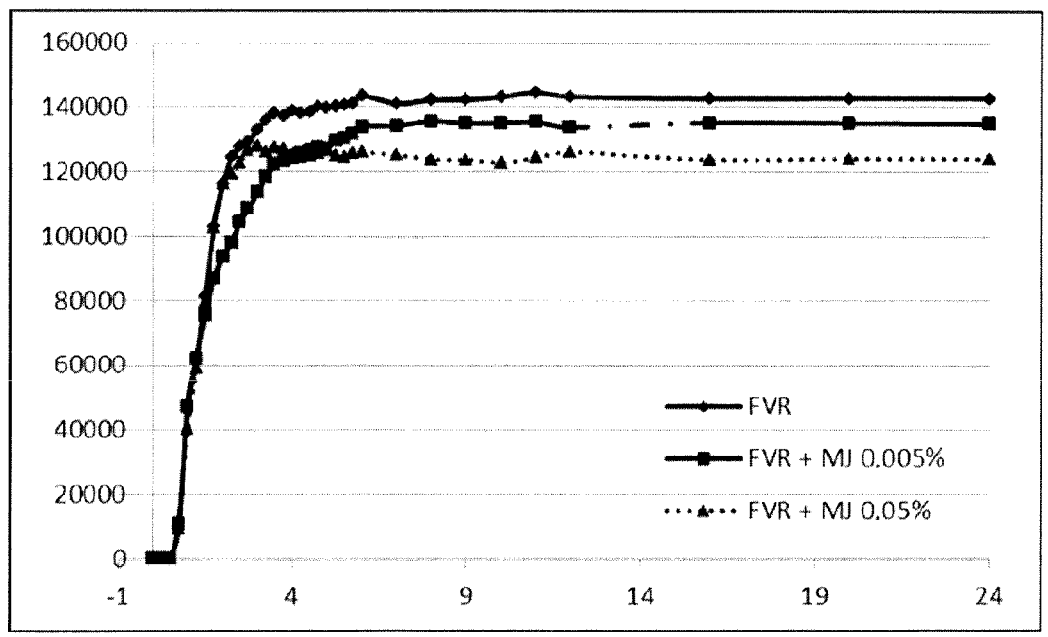
FIG. 1B shows contractile forces developed by red stretch mark fibroblasts (FVR) in the presence or absence of *Passiflora* concentrate (MJ) in a dermal equivalent tensioned in the GlaSbox® system (total curves).

The red stretch mark fibroblasts developed significantly more contractile forces than the adjacent healthy skin fibroblasts (results not shown). The *Passiflora* concentrate significantly reduced the contractile forces generated by the red stretch mark fibroblasts (FIGS. 1A and 1B).

FIG. 1: Contractile forces developed by red stretch mark fibroblasts (FVR) in the presence or absence of *Passiflora* concentrate (MJ) in a dermal equivalent tensioned in the GlaSbox® system.

A: details of initial 6 hours; B: total curves

Statistics: Two-factor variance analysis followed by Fisher test

° FVR; ∇ FVR+MJ 0.005%; □ FVR+MJ 0.05% x-axis: time in hours; y-axis: forces (arbitrary unit/million cells)

Analysis of Glasbox® curves (Table 11) shows that the area under curve AUC, maximum contraction and slope are significantly reduced in the presence of the *Passiflora* concentrate which therefore not only reduces the contractile forces but also the rate of contraction of the red stretch mark fibroblasts.

TABLE 11

Analysis of Glasbox ® curves: AUC, maximum contraction and slope.

| | FVR | | FVR + MJ 0.005% | | FVR + MJ 0.05% | |
| --- | --- | --- | --- | --- | --- | --- |
| | Mean | SEM | Mean | SEM | Mean | SEM |
| AUC | 3055456 | 29596 | 2992140 | 31251 | 2823517\*\*\*,aa | 33363 |
| Max | 140095 | 2412 | 128206\*\* | 1928 | 126302\*\* | 1892 |
| Slope | 2.29 | 0.04 | 1.39\*\*\* | 0.04 | 1.18\*\*\*,aa | 0.04 |

\*\*$p < 0.01$;
\*\*\*$p < 0.001$ vs FVR; $^{aa}p < 0.01$ vs MJ 0.005%
One-factor variance analysis followed by Fisher test

4. Conclusion

These results show the anti-stretch mark effect of the *Passiflora* concentrate, through its action on reducing the contractile forces generated by red stretch mark fibroblasts and its re-densifying effect on the dermal matrix.

C. Slimming Effect: Effect on Lipolysis of Human Adipose Tissue

Human white adipose tissue carries out a fundamental metabolic function by providing the other tissues in the body with energy molecules in the form of fatty acids released by the adipocyte lipolysis process: adipocytes mobilise energy reserves by hydrolysing stored triglycerides to fatty acids and glycerol; the fatty acids thus released into the bloodstream can be used by other tissues for energy purposes. The effect of the *Passiflora* concentrate on adipocyte lipolysis was evaluated by assay of glycerol released during hydrolysis of the triglycerides stored in human mature adipocytes cultured in 3 dimensions.

a. Material and Methods

Mature adipocytes, derived from biopsies of subcutaneous adipose tissue taken from five donors (normal-weight or overweight) were isolated and encapsulated in peptide gel allowing their survival and biological functionality in culture. The encapsulated mature adipocytes were incubated in the presence of 0.001% or 0.005% *Passiflora* concentrate, or 10 μM forskoline (standard) for 4 hours.

After incubation, the released glycerol was assayed in the culture medium using an assay kit (Randox), the values obtained were normalised with the amount of DNA evaluated with a kit (Invitrogen).

b. Results

The release of glycerol by the adipocytes was increased with the *Passiflora* concentrate in each of the 5 donors examined. Table 6 gives the mean of the effect observed in the 5 donors: the *Passiflora* concentrate significantly stimulated the release of glycerol, it therefore promotes adipocyte lipolysis to the benefit of a slimming effect.

TABLE 12

Lipolytic effect of the *Passiflora* concentrate evaluated via release of glycerol by mature adipocytes. Mean ± standard deviation of 5 donors.

|  | Control | Forskoline (standard) | *Passiflora* concentrate 0.001% | *Passiflora* concentrate 0.005% |
|---|---|---|---|---|
| Release of glycerol (Arbitrary unit) | 1.00 ± 0.00 | 6.60 ± 1.54 | 1.40 ± 0.38 | 1.78 ± 0.30 |
| Stimulation (%) |  | +660% ** | +40% ns | +78% ** |

** $p < 0.01$ - Wilcoxon/Kruskal Wallis non-parametric test

The invention claimed is:

1. A method to stimulate, restore or regulate the metabolism of skin or mucosa cells or to treat disorders related to dermal tissue, or a combination of thereof, comprising topically administering to a person in a need thereof a lipid extract from *Passiflora* seeds selected from *Passiflora incarnate* seeds, *Passiflora edulis* seeds, and a combination thereof, wherein said lipid extract is oil of *Passiflora* seeds concentrated in its unsaponifiable fraction containing 3 to 100 weight % of unsaponifiables relative to the total weight of the extract, wherein the lipid extract acts:
   as anti-aging agent,
   as healing agent,
   to prevent deterioration of and/or to maintain homeostasis of the skin or mucosae,
   as antioxidant agent,
   as anti-inflammatory agent,
   as slimming or anti-cellulite agent,
   to prevent or treat skin stretch marks, or
   as depigmenting agent.

2. A method according to claim 1 for preventing or delaying premature skin ageing.

3. A method according to claim 2 for preventing or delaying photo-induced premature skin ageing.

4. A method according to claim 1 for preventing, reducing or treating wrinkles, lines or microrelief deterioration, or a combination thereof.

5. A method according to claim 2 for reinforcing the mechanical properties of the skin and mucosae, or reinforcing or restoring skin elasticity or firmness, or a combination of these indication.

6. A method according to claim 5 for combating withered, flabby, slackened, sagging or thinned skin, or a combination thereof.

7. A method according to claim 1 for promoting healing.

8. A method according to claim 1 for preventing or treating pathologies or conditions selected from the group formed by surface scarring, fragile lips and cheilitis, stretch marks, skin after stings and bites, skin abrasions, skin spots or skin scabs, and fragile and sensitive skin, or a combination thereof.

9. A method for cosmetic care or cosmetic treatment for the skin, skin appendages, mucosae, or a combination thereof, to improve the condition or appearance thereof, comprising administering topically a lipid extract from *Passiflora* seeds selected from *Passiflora incarnate* seeds, *Passiflora edulis* seeds, and a combination thereof, wherein said lipid extract is oil of *Passiflora* seeds concentrated in its unsaponifiable fraction containing 3 to 100 weight % of unsaponifiables relative to the total weight of the extract.

10. A method for cosmetic care according to claim 9 for improving firmness, elasticity or tonicity of the skin.

11. A method for cosmetic treatment according to claim 9 for dry skin with feeling of tightness.

12. A method for cosmetic treatment according to claim 9 for remodeling the silhouette, limiting "orange peel" effect.

13. The method according to claim 1, wherein said lipid extract is oil of Passiflora seeds concentrated in its unsaponifiable fraction containing 4 to 100 weight % of unsaponifiables relative to the total weight of the extract.

14. The method according to claim 9, wherein said lipid extract is oil of Passiflora seeds concentrated in its unsaponifiable fraction containing 4 to 100 weight % of unsaponifiables relative to the total weight of the extract.

15. A method to stimulate, restore or regulate the metabolism of skin or mucosa cells or to treat disorders related to dermal tissue, or a combination thereof, comprising orally administering to a person in a need thereof a lipid extract from *Passiflora* seeds selected from *Passiflora incarnate* seeds, *Passiflora edulis* seeds, and a combination thereof, wherein said lipid extract is oil of Passiflora seeds concentrated in its unsaponifiable fraction containing 4 to 100 weight % of unsaponifiables relative to the total weight of the extract, wherein the extract acts:
   as anti-aging agent,
   as healing agent,
   to prevent deterioration of and/or to maintain homeostasis of the skin or mucosae,
   as antioxidant agent,
   as anti-inflammatory agent,
   as slimming or anti-cellulite agent,
   to prevent or treat skin stretch marks, or
   as depigmenting agent.

16. A method for cosmetic care or cosmetic treatment for the skin, skin appendages, mucosae, or a combination thereof to improve the condition or appearance thereof, comprising orally administering to a person in a need thereof a lipid extract from *Passiflora* seeds seleted from *Passiflora incarnate* seeds, *Passiflora edulis* seeds, and a combination thereof, wherein said lipid extract is oil of *Passiflora* seeds concentrated in its unsaponifiable fraction containing 4 to 100 weight % of unsaponifiables relative to the total weight of the extract.

17. The method for cosmetic care according to claim 16, wherein the method is for improving firmness, elasticity or tonicity of the skin, for dry skin with feeling of tightness, or for remodeling the silhouette, limiting "orange peel" effect.

* * * * *